United States Patent [19]

Baker et al.

[11] Patent Number: 5,055,596

[45] Date of Patent: Oct. 8, 1991

[54] DERIVATIVES OF AVERMECTIN AND MILBEMYCIN

[75] Inventors: Geoffrey H. Baker, Epsom; Roderick J. Dorgan, Epsom; David O. Morgan, Epsom; Rhona M. Banks, Tadworth; Simon E. Blanchflower, Tadworth; Mark E. Poulton, Tadworth; Peter R. Shelley, Betchworth, all of England

[73] Assignee: Beecham Group p.l.c., Brentford, England

[21] Appl. No.: 559,989

[22] Filed: Jul. 30, 1990

Related U.S. Application Data

[63] Continuation of Ser. No. 265,509, Nov. 1, 1988, abandoned.

[30] Foreign Application Priority Data

Nov. 3, 1987 [GB] United Kingdom ............... 8725679
Aug. 2, 1988 [GB] United Kingdom ............... 8818374
Oct. 21, 1988 [GB] United Kingdom ............... 8824763

[51] Int. Cl.$^5$ ............................................. C07D 493/22
[52] U.S. Cl. ................................. 549/268; 549/214; 549/264; 536/7.1
[58] Field of Search .................... 549/268, 264, 214; 536/7.1; 514/450

[56] References Cited

U.S. PATENT DOCUMENTS

4,285,963 8/1981 Arison et al. ................... 514/455

FOREIGN PATENT DOCUMENTS

| | | |
|---|---|---|
| 0073660 | 3/1983 | European Pat. Off. ............. 536/7.1 |
| 0074758 | 3/1983 | European Pat. Off. . |
| 0170006 | 2/1986 | European Pat. Off. ............. 549/264 |
| 0214731 | 7/1986 | European Pat. Off. ............. 536/7.1 |
| 0194125 | 9/1986 | European Pat. Off. ............. 549/264 |
| 0204421 | 12/1986 | European Pat. Off. ............. 549/264 |
| 0212867 | 3/1987 | European Pat. Off. ............. 536/7.1 |
| 0237339 | 9/1987 | European Pat. Off. ............. 549/264 |
| 0241146 | 10/1987 | European Pat. Off. ............. 549/264 |
| 0288205 | 10/1988 | European Pat. Off. . |
| 0254853 | 1/1989 | European Pat. Off. ............. 549/264 |
| 1390336 | 4/1975 | United Kingdom ............... 549/264 |
| 2170499 | 8/1986 | United Kingdom ............... 549/264 |

OTHER PUBLICATIONS

*J. Antibiotics,* 29 (3), 76-14-76-15 (1976).
*J. Antibiotics,* 29 (6), 76-35-76-42 (1976).

*Primary Examiner*—Richard L. Raymond
*Assistant Examiner*—Mark W. Russell
*Attorney, Agent, or Firm*—Hopgood, Calimafde, Kalil, Blaustein & Judlowe

[57] ABSTRACT

Compounds of formula (I):

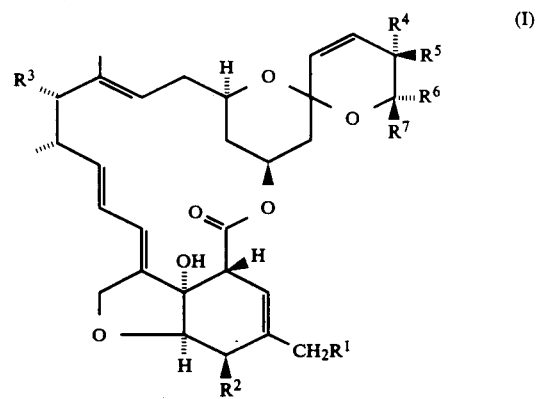

wherein $R^1$ is hydrogen or optionally protected hydroxy; $R^2$ is alkoxy, optionally protected hydroxy, oxo or optionally O-substituted oximino; $R^3$ is hydrogen, optionally protected hydroxy, or a group 4'-(α-L-oleandrosyl)-α-L-oleandrosyloxy or α-L-oleandrosyloxy wherein the terminal hydroxy group is optionally protected; one or $R^4$ and $R^5$ is hydrogen and the other is methyl; and one of $R^6$ and $R^7$ is hydrogen and the other is methyl; with the proviso that (a) when $R^1$ is optionally protected hydroxy, $R^3$ is hydrogen, and (b) when $R^2$ is not methoxy or optionally protected hydroxy, $R^1$ and $R^3$ are both hydrogen, are new and useful as anthelmintic agents.

2 Claims, No Drawings

DERIVATIVES OF AVERMECTIN AND MILBEMYCIN

This application is a continuation of application Ser. No. 265,509, filed Nov. 1, 1988, now abandoned.

The present invention relates to novel anthelmintic compounds, to processes for their production, to pharmaceutical formulations containing them, and to their use in human or veterinary medicine.

The milbemycins and avermectins are a group of macrolide antibiotics which have been prepared by the cultivation of microorganisms and are described in inter alia GB-A-1,390,336, J. Antibiotics 29(3), 76-14 to 76-16 and 29 (6), 76-35 to 76-42, GB-A-2 170 499, EP-A-0 073 660 and EP-A-0 204 421. They have anthelmintic activity. Further anthelmintically active milbemycins and avermectins are described in GB-A-2 176 180, EP-A-0 212 867, EP-A-0 237 339, EP-A-0 241 146, EP-A-0 214 731, EP-A-0 194 125, EP-A-0 170,006, and U.S. Pat. No. 4,285,963.

The compounds disclosed in the above references include compounds of formula (A):

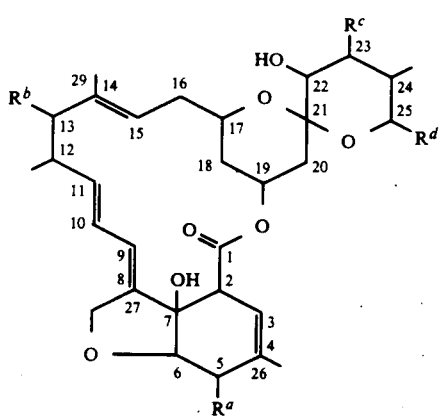

wherein $R^a$ is methoxy or hydroxy, $R^b$ is hydrogen, $R^c$ is hydrogen, pentanoyloxy, heptanoyloxy, or 2-methylhexanoyloxy, and $R^d$ is methyl or ethyl, with the proviso that when $R^c$ is hydrogen, $R^e$ is methoxy; or $R^a$ is methoxy or hydroxy, $R^b$ is hydrogen, $R^c$ is 2-methylbutanoyloxy, 2,4-dimethylpent-2-enoyloxy, or 2,4-dimethylpentanoyloxy, and $R^d$ is methyl or ethyl, with the proviso that when $R^d$ is ethyl, $R^a$ is hydroxy and $R^c$ is 2,4-dimethylpentanoyloxy; or $R^a$ is methoxy or hydroxy, $R^b$ is the group of formula:

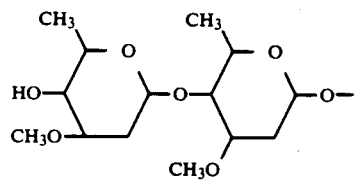

(4'-(α-L-oleandrosyl)-α-L-oleandrosyloxy), $R^c$ is hydroxy, and $R^d$ is 1-methyl propyl.

EP-A-0 254 583 (U.S. Ser. No. 076,274) describes compounds of formula (B):

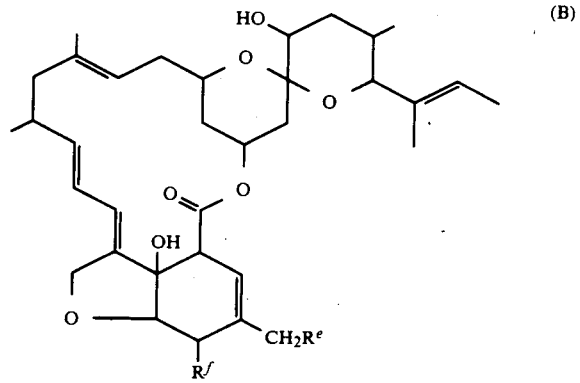

wherein $R^e$ is hydrogen or E 2-methyl 2-butenoyloxy, and $R^f$ is methoxy or hydroxy, with the proviso that when $R^e$ is E 2-methyl 2-butenoyloxy, $R^f$ is methoxy.

The microorganism from which the compounds of formula (B) were obtained has also been found to produce compounds of formula (C)

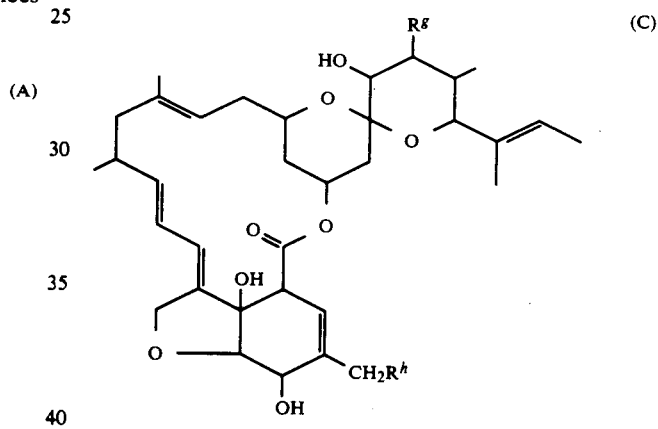

wherein $R^g$ and $R^h$ are as set out in the following table:

| Compound | $R^g$ | $R^h$ |
|---|---|---|
| VM48130 | O—CO—CH(CH₃)₂ | H |
| VM48633 | H | O—CO—CH=C(CH₃)₂ |
| VM47704 | H | O—CO—CH₂—CH(CH₃)₂ |

EP-A-0 288 205 (U.S. Ser. No. 183,581) discloses compounds of formula (D):

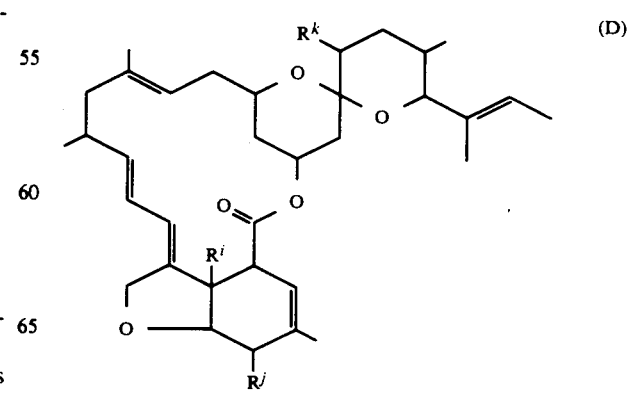

wherein R$^i$ is hydroxy or methoxy and R$^j$ and R$^k$ are the same or different and each is selected from optionally protected hydroxy, alkoxy, acyloxy, sulphonyloxy, oxo and optionall O-substituted oximino.

The absolute configuration of the compounds of formulae (A) to (D) is believed to be as follows:

drosyl)-α-L-oleandrosyloxy or α-L-oleandrosyloxy wherein the terminal hydroxy group is optionally protected; one of R$^4$ and R$^5$ is hydrogen and the other is methyl; and one of R$^6$ and R$^7$ is hydrogen and the other is methyl; with the proviso that (a) when R$^1$ is optionally protected hydroxy, R$^3$ is hydrogen, and (b) when

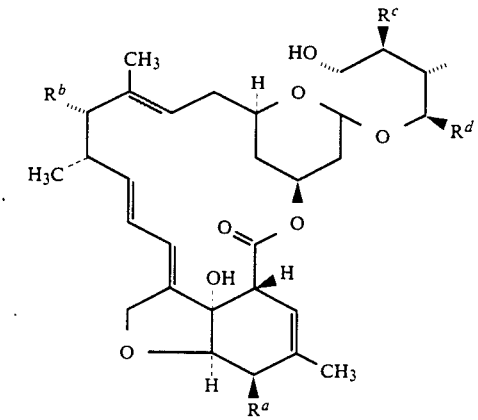

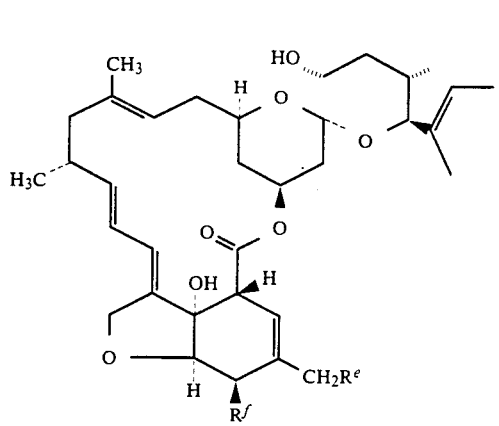

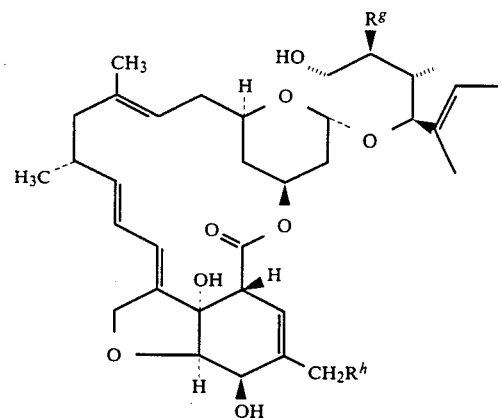

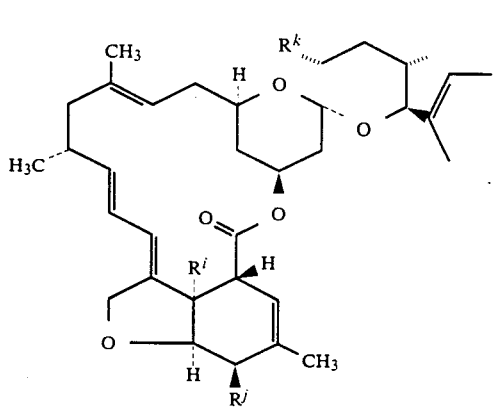

We have now discovered that it is possible to prepare novel compounds from starting materials having a hydroxy substituent at the C-22 position, and that these compounds are useful s anthelmintically active compounds.

According to the present invention there is provided a compound of formula (I):

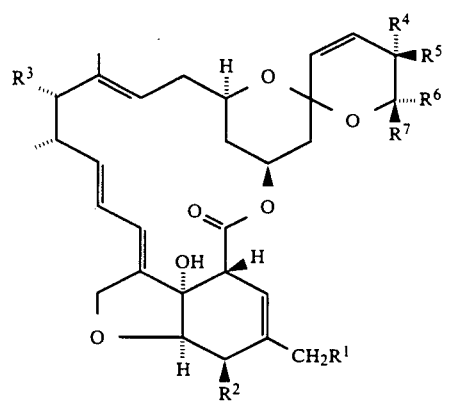

wherein R$^1$ is hydrogen or optionally protected hydroxy; R$^2$ is alkoxy, optionally protected hydroxy, oxo or optionally O-substituted oximino; R$^3$ is hydrogen, optionally protected hydroxy, or a group 4'-(α-L-olean- R$^2$ is not methoxy or optionally protected hydroxy, R$^1$ and R$^3$ are both hydrogen.

Suitable protecting groups for hydroxy include TBDMS (t-butyldimethylsilyl), and acyl. Further suitable protecting groups are described in, for example, "Protective Groups in Organic Synthesis" Theodora W. Greene, Wiley-Interscience 1981 Ch 2, 10–86.

Suitable substituents for an oxime are as set out in EP-A-O 288 205. Compounds of the present invention having at least one oxo group may be converted to a corresponding optionally O-substituted oxime by conventional means, for example by reaction with optionally O-substituted hydroxylamine, for example in the form of the hydrochloride, in a suitable solvent such as aqueous methanol, typically at ambient temperatures. Once formed an O-substituted oxime may be reacted with a suitable O-acylating or O-alkylating agent. The compound may exist as syn or anti isomers or mixtures thereof. Suitable etherifying substituents for an oxime include C$_{1-6}$ alkyl and C$_{2-6}$ alkenyl.

The compound or mixture of compounds according to the invention is suitably provided in substantially pure form, for example at least 50% pure, suitably at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

The compounds of the invention have parasiticidal properties, for example against nematodes such as *Trichostronqvlus colubriformis*, and are useful for the treatment of helminthiasis in animals such as mammals, including humans and domesticated animals (including farm animals).

Accordingly the present invention also provides a compound according to the invention, for use in the treatment of the human or animal body, especially for treating endo- and ectoparasitic infestations and particularly for treating helminthiasis of domestic and farm animals.

The term helminthiasis encompasses those diseases of man and animals caused by infestation with parasitic worms such as Strongyles, Ascarids, hookworms lungworms, filarial worms and whipworms. The compound may also be used against nematodes occurring in the soil or parasitic to plants.

The compounds of the invention are also active against Arthropods. The phylum Arthropoda comprises insects—such as biting flies, lice, bugs, beetles and fleas— and arachnids—such as mites and ticks.

Thus, a broad aspect of the invention provides a method of eradicating arthropod or nematode infestations, which method comprises applying a compound according to the invention or a derivative thereof to the arthropods or nematodes or to their environment.

The present invention thus provides a pesticidal composition comprising a compound according to the invention or a derivative thereof together with a suitable carrier or excipient, such as an aerosol formulation.

The present invention also provides a pharmaceutical or veterinary composition comprising a compound according to the invention or a pharmaceutically acceptable derivative thereof together with a pharmaceutically or veterinarily acceptable carrier or excipient.

The present invention also provides a method of treatment or prophylaxis of endo- and ectoparasitic infestations, especially helminthiasis, of animals, especially humans and domesticated mammals, which comprises administering an effective non-toxic amount of a compound according to the invention or a pharmaceutically acceptable derivative thereof, or a composition according to the invention, to a patient in need thereof.

The composition according to the invention may be formulated for administration in any convenient way for use in human or veterinary medicine, by analogy with other anthelmintics.

In suitable formulations the drug may be administered to animals orally (as a paste, drench, bolus, capsule or tablet), parenterally, percutaneously, as a food additive (e.g. granules, pellets or powder), or may be prepared as an aerosol spray formulation.

The compounds of the invention may be formulated as a mixture with each other and/or with other anthelmintics, insecticides, acaricides or other pharmacologically active substances.

Suitably the composition consists of sufficient material to provide a dose of from 0.01 to 100 mg of active ingredient per kg of animal body weight per dose, more suitably 1.0 to 100 mg/kg per dose.

A composition according to the invention may suitably contain from 0.1% by weight, preferably from 1.0 to 60% by weight, of the compound according to the invention (based on the total weight of the composition), depending on the method of administration.

It will be appreciated that, in some cases, it will be advisable to repeat the dosing of the infected or potentially infected human or animal with the compound of the invention according to conventional dosage regimes used with anthelmintics.

A further aspect of the invention provides a process for the preparation of a compound of formula (I), which process comprises the acid catalysed cyclisation of a compound of formula (II):

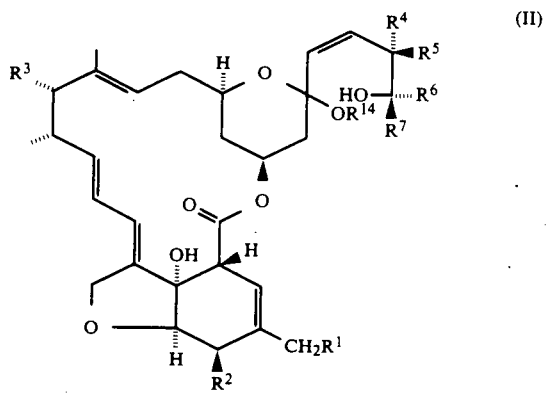

wherein $R^1$ to $R^7$ have the values set out above, and $R^{14}$ is hydrogen or lower alkyl, more particularly $C_{1-3}$ alkyl.

It should be appreciated that the configuration at C21 of the compound of formula (I) will be subject to thermodynamic control (as discussed e.g. by P. Deslongchamps et al, Canadian J. Chem. [1981] 59, 1105): it is believed that the epimer in which the configuration at C21 is as in the naturally occurring compounds of formulae (A), (B) and (C) is normally thermodynamically favoured.

Compounds of formula (II) may be obtained from compounds of formula (III):

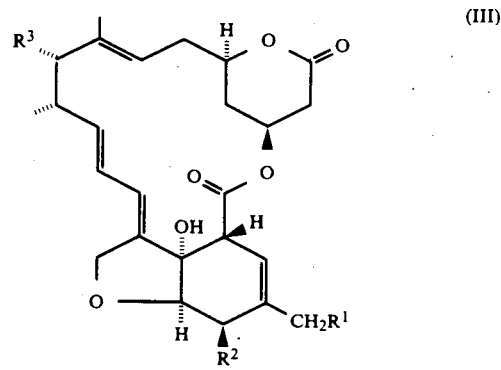

wherein $R^1$ to $R^3$ are as defined above, via the routes shown in Scheme I below:

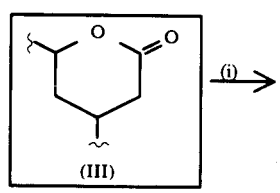

-continued

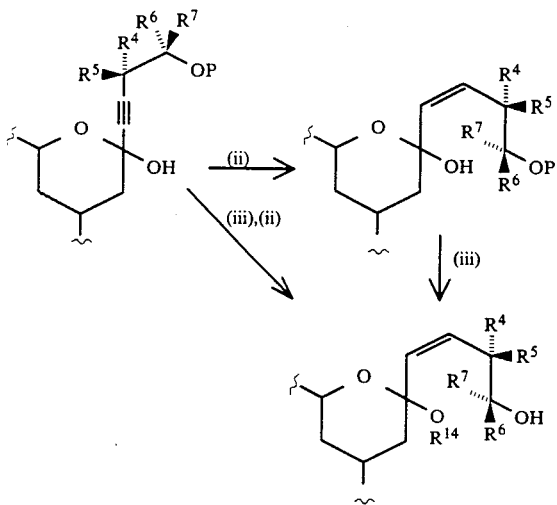

Notes
(i) MC≡C.CR⁴R⁵.CR⁶R⁷OP where M is a metalating agent such as Li or BrMg and P is an acid labile protecting group such as THP (tetrahydropyranyl)
(ii) H₂/Lindlar catalyst or other suitable catalyst
(iii) R¹⁴OH/H+

The compounds of formula (III) are novel and form a further aspect of the invention.

Compounds of formula (III) can be prepared by cleaving the 21-22 carbon-carbon bond of a precursor having a hydroxy substituent on C22, such as compounds of formulae (A), (B), (C) and (D).

Thus, a process for the preparation of a compound of formula (III) comprises subjecting a compound of formula (IV):

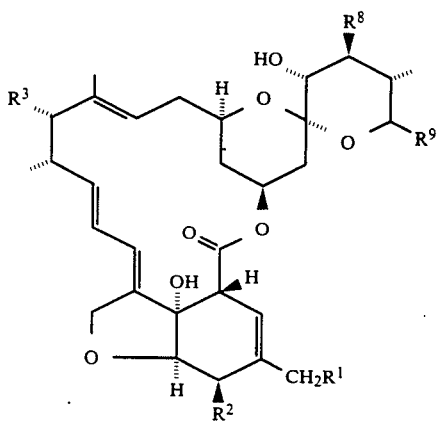

to 21-22 carbon-carbon bond cleavage, wherein $R^1$, $R^2$ and $R^3$ are as defined above with respect to formula (I), $R^8$ is hydrogen or optionally protected hydroxy, and $R^9$ is methyl, ethyl, 1-methyl propyl or (Z) but-2-en-2-yl, with the proviso that (a) if $R^1$ is optionally protected hydroxy, then $R^3$ is hydrogen, $R^8$ is hydrogen, and $R^9$ is (Z) but-2-en-2-yl, (b) if and only if $R^3$ is not hydrogen then $R^9$ is 1-methyl propyl, (c) if $R^3$ is not hydrogen, then $R^8$ is optionally protected hydroxy, (d) if $R^9$ is (Z) but-2-en-2-yl and $R^8$ is optionally protected hydroxy, then $R^1$ is hydrogen and $R^2$ is optionally protected hydroxy, and (e) if $R^2$ is not methoxy or option- ally protected hydroxy, then $R^1$, $R^3$ and $R^8$ are hydrogen and $R^9$ is (Z) but-2-en-2-yl.

Particular protecting groups for $R^1$ and $R^8$ when they are protected hydroxy include those present in the naturally occurring compounds of formulae (A) to (C) above.

Those skilled in the art will appreciate that acyl can readily be removed, for example by base hydrolysis, and compounds of formula (I) wherein $R^1$ is hydroxy or protected hydroxy, wherein the protecting group may or may not be acyl, $R^2$ is methoxy or optionally protected hydroxy, and $R^3$ is hydrogen, are thus readily derivable from the corresponding compounds of formulae (B) and (C) wherein $R^1$ is a naturally occurring acyloxy group.

It will further be appreciated that 4′-(α-L-oleandrosyl)-α-L-oleandrosyl may readily be removed or partly removed, for example by acid hydrolysis, and compounds of formula (I) wherein $R^3$ is optionally protected hydroxy, or α-L-oleandrosyloxy, wherein the terminal hydroxy group is optionally protected, may thus readily be derived from the compounds of formula (A) wherein $R^b$ is 4-(α-L-oleandrosyl)-α-L-oleandrosyloxy.

In a preferred process of the invention, $R^1$ is hydrogen, $R^2$ is methoxy or hydroxy, $R^3$ and $R^8$ are hydrogen, and $R^9$ is (Z) but-2-en-2-yl.

Processes for cleaving the 21-22 carbon-carbon bond will typically include oxidation of the C22 hydroxy group to a ketone, conversion of the ketone to a corresponding oxime, and effecting rearrangement of the oxime under Beckmann conditions. The Beckmann rearrangement is discussed in "The Chemistry of the carbon-nitrogen double bond" Ed. Saul Patai Wiley-Interscience 1970, 408.

The oxidation will typically be carried out using DMSO/oxalyl chloride (Swern oxidation), or a chromium based oxidizing agent such as pyridinium chlorochromate (PCC), with protection of hydroxy groups elsewhere as necessary, for example using TBDMS.

The oxime may then be prepared by any conventional means, for example by reaction with optionally O-substituted hydroxylamine, for example in the form of the hydrochloride, in a suitable solvent such as aqueous methanol, typically at ambient temperatures.

The oxime may be used directly in the Beckmann rearrangement or may first be converted to a more reactive derivative, for example by sulphonylation with an appropriate sulphonylating agent such as a sulphonic anydride or sulphonyl halide, advantageously in the presence of a little of the corresponding sulphonic acid.

The Beckmann rearrangement is typically effected using an acid catalyst such as PPSE (polyphosphoric acid silyl ether). Where the oxime has been activated, for example by sulphonylation, mildly acidic work-up conditions can be used to effect the rearrangement In any or all of the above processes, sensitive groups may if necessary be protected using protecting groups which are conventional in the art.

It should be appreciated that in the presence of an alcohol the valerolactone compound of formula (III) will exist in equilibrium with the corresponding ring opened ester.

Those skilled in the art will appreciate that the process of the invention can be applied to essentially any milbemycin or avermectin having a hydroxy (or oxo or oxime) group present at the C22 position. Furthermore, the compounds of formulae (I) and (III) can be further modified using techniques which are in themselves well known in the art and are described in, for example, Natural Products Reports 3 (2) [1986]87 et seq. and Macrolide Antibiotics [1984] Ch. 14, 553 et seq. Thus, a broad aspect of the invention provides any milbemycin or avermectin of partial formula (i) hereinbelow, as well as a process for its preparation which comprises effecting acid-catalysed cyclisation of a milbemycin or avermectin of partial formula (ii) hereinbelow:

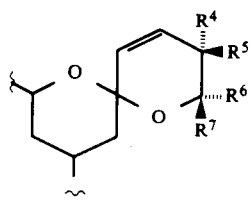
(i)

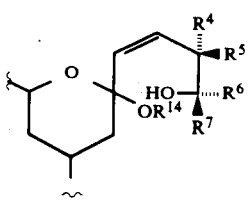
(ii)

wherein $R^4$ to $R^7$ and $R^{14}$ have the values set out above.

A further broad aspect of the invention provides a milbemycin or avermectin of partial formula (v) hereinbelow, as well as a process for its preparation which comprises effecting 21-22 carbon-carbon bond cleavage of a milbemycin or avermectin having a hydroxy (or oxo or oximino) substituent at the C22 position:

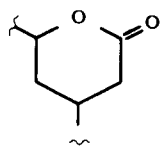
(v)

The following Examples illustrate the present invention. VM 44864 and VM 44866 are the compounds of formula (IV) wherein $R^1$ is hydrogen, $R^3$ and $R^8$ are both hydrogen, $R^9$ is (Z) but-2-en-2-yl, and $R^2$ is methoxy and hydroxy respectively. VS 47709 is the compound of formula (III) wherein $R^1$ and $R^3$ are both hydrogen and $R^2$ is methoxy.

Compound 6 of GB-A-2 170 499 is the compound of formula (A) wherein Ra is methoxy, $R^b$ is hydrogen, $R^c$ is 2,4-dimethylpentanoyloxy and $R^d$ is methyl. "X" represents the following structure:

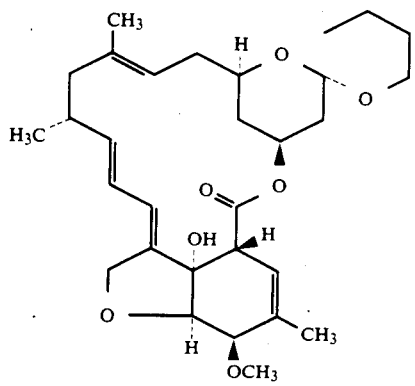

EXAMPLE 1

(a) 22-Keto VM 44864

To a solution of oxalyl chloride (0.05 ml) in dry dichloromethane (1 ml) at −70°, under a nitrogen atmosphere, was added dropwise a solution of dimethylsulphoxide (0.05 ml) in dry dichloromethane (1 ml). To this solution was added dropwise a solution of VM 44864 (8 mg), prepared as described in Example 2 of EP-A-0 254 583 (U.S. Ser. No. 076,274), in dry dichloromethane (0.5 ml) and the resulting solution stirred at −70° for 1.5 h. A solution of triethylamine (0.2 ml) in dry dichloromethane (1 ml) was added, the mixture allowed to warm to room temperature whilst stirring for 1.25 h, and the mixture poured onto a 1:1 mixture of cold water and ether. The layers were separated, the aqueous layer extracted with ether and the combined ether extracts washed with water, brine, and dried ($MgSO_4$). The ether was evaporated and the product purified by preparative thin. layer chromatography (Analtech silica taper plate eluted with methanol/dichloromethane 2:98) to give the title compound (1.4 mg), max ($CH_3OH$) 244 nm, m/z (FAB Na+/Noba) (relative intensity) 619 [MNa]+ (100%).

(b) 22-oximino derivative of VM 44864

To a solution of 22-keto VM 44864 (18 mg) in methanol (5 ml) was added dropwise a solution of hydroxylammonium chloride (24 mg) is water (1 ml). The resulting solution was stirred at room temperature for 15 minutes before evaporation at reduced pressure to remove the methanol. Water (15 ml) and ether (15 ml) were added and the ether layer was evaporated, extracted with water (15 ml), dried ($MgSO_4$) and evaporated. The crude product was purified by preparative thin layer chromatography (silica eluted with 595 MeOH/$CH_2Cl_2$) to give the title compound (10 mg) $m/z$ (FAB Na+/Noba) (relative intensity)634 [MNa]+ 100%

$\delta_c$ ($CDCl_3$), 173.8, 156.8, 142.4, 139.8, 137.3, 135.9, 133.7, 124.1, 123.5, 120.5, 119.5, 118.5, 98.0, 81.9, 80.4, 77.6, 76.9, 68.7, 68.4, 68.3, 57.8, 48.5, 45.7, 36.4, 35.9, 35.8, 34.5, 32.9, 27.1, 22.4, 19.9, 17.7, 15.6, 13.2, 10.9 ppm.

(c) Lactone VS 47709

To a solution of pyridine (1 ml) in dichloromethane (20 ml) at −30° was added triflic anhydride (0.2 ml) followed by the 22-oximino derivative of 22-keto VM 44864 (37 mg). After stirring at −30° for 2 hours, the solution was allowed to warm to 5° and poured onto 2M hydrochloric acid. After shaking with the acid, the dichloromethane layer was separated, dried (MgSO$_4$), and evaporated. The crude product was purified by preparative thin layer chromatography (silica eluted with ether) to give the title lactone (5mg). The $^{13}$C n.m.r. (CDCl$_3$) spectrum showed the following signals, 172.9, 168.4, 142.6, 139.9, 139.1, 136.4, 123.6, 119.5, 118.8, 118.0, 80.6, 77.8, 76.7, 76.6, 68.1, 66.1, 57.8, 48.4, 45.6, 36.8, 35.9, 34.6, 34.1, 22.3, 19.9, and 15.7.

EXAMPLE 2

(a) 5-TBDMS-protected VM 44866

A mixture of VM 44866 (10.9 mg), prepared as described in Example 3 of EP-A-0 254 583 (U.S. Ser. No. 076,274), imidazole (20 mg), t-butyldimethylsilylchloride (30 mg) and anhydrous dimethylformamide (5 ml) was stirred at 20° C. for 16 h in an atmosphere of nitrogen. To the mixture was added t-butyldimethylsilylchloride (30 mg), imidazole (20 mg) and stirring continued at 21° C. for 5 h. The mixture was poured onto water (10 ml) and extracted with ether (2×5 ml). The combined ether extracts were washed with water (10 ml), dried (MgSO$_4$) and evaporated to give an oil. This residue was purified by preparative thin layer chromatography (silica; ether/hexane 30/70) to give two products.

Product.1. 5-t-butyldimethylsilyl VM44866 (6.0 mg); t.l.c. R$_f$=0.33 ether/hexane 1:1 SiO$_2$; M/$_z$(FAB Na+/-Noba) (relative intensity) 721 (100%) [MNa]+

Product.2. 5,22-di-t-butyldimethylsilyl VM44866 (1.0 mg); t.l.c. R$_f$=0.66 ether/hexane 1:1 SiO$_2$; M/$_z$ (FAB Na+/Noba) (relative intensity) 835 (100%) [MNa]+

5-TBDMS-protected 22-keto VM 44866

A solution of oxalyl chloride (0.12 ml) in dry dichloromethane (2 ml) at −70° C. under nitrogen was treated dropwise with a solution of dimethylsulphoxide (0.1 ml) in dry dichloromethane (2 ml) and then dropwise with a solution of 5-t-butyldimethylsilyl VM 44866 (46 mg) in dry dichloromethane (1.0 ml). The resulting solution was stirred at −70° for 1.5 h before being treated dropwise with a solution of triethylamine (0.4 ml) in dry dichloromethane (1 ml). The reaction mixture was stirred for 1 h without cooling and poured onto a mixture of cold water and ether (1:1). The aqueous layer was extracted with ether. The combined organic layers were washed with water, dried (MgSO$_4$) and evaporated. The residue was chromatographed over silica using dichloromethane increasing to dichloromethane/methanol 98:2 to give the title compound (16 mg) which was deprotected as described below.

(c) 22-Keto VM 44866

A solution of 5-t-butyldimethylsilyl-22-keto VM 44866 (16 mg) in methanol (5 ml) was treated with p-toluenesulphonic acid (10 mg) and the mixture stirred for 1.5 h at 21° C. The mixture was then evaporated to dryness before addition of water (10 ml) and ether (10 ml). After separation, the ether layer was washed with water (10 ml), dried (MgSO$_4$) and evaporated to give an oil. This residue was purified by preparative thin layer chromatography (silica: dichloromethane/methanol 98:2) to give the title compound (10 mg) M/$_z$ (FAB Na+/Noba) (relative intensity) 605 (100%) [MNa]+ δ$_c$ (CDCl$_3$), 202.5, 173.7, 142.7, 139.7, 137.9, 137.7, 133.2, 124.9, 123.5, 120.3, 120.2, 118.0, 99.2, 81.8, 80.2, 79.2, 69.1, 68.5, 68.4, 67.8, 48.5, 45.7, 43.3, 37.1, 36.3, 36.0, 34.6, 33.9, 22.4, 19.9, 18.2, 15.6, 13.3, 10.9, ppm.

(d) 5-TBDMS-22-hydroxyimino VM 44866

The title compound was prepared from 5-TBDMS-22-keto VM 44866 in a similar procedure to that described in Example 1(b).

(e) 5-TBDMS-de-O-methyl VS 47709 and 5-de-O-methyl VS 47709

To a stirred solution of 5-TBDMS-22-hydroxyimino VM 44866 (1.5 g) and triethylamine (1.0 g) in dichloromethane (10 ml) at 0° C. was added portionwise 4-nitrobenzenesulphonyl chloride (0.94 g). The mixture was allowed to warm to room temperature before the addition of water (10 ml). The dichloromethane layer was separated, washed with water (10 ml), dried (MgSO$_4$) and evaporated. To a solution of the residue, in tetrahydrofuran (50 ml), was added 4-toluenesulphonic acid (1.0 g) and the mixture was stirred at room temperature for 3 h. The mixture was then evaporated to dryness before addition of dichloromethane (25 ml) and aqueous sodium bicarbonate solution (25 ml). After separation, the dichloromethane layer was washed with water (20 ml), dried (MgSO$_4$) and evaporated to give an oil. This residue was purified by column chromatography (silica eluted with hexane/ether) to give the title products.

5-TBDMS-de-O-methyl VS 47709 (200 mg), m/z (FAB Na+/Noba) (relative intensity) 581 [MNa]+ (100%) and 5-de-O-methyl VS 47709 (450 mg), m/z (FAB Na+/Noba) (relative intensity) 467 [MNa]+ (100%), δ$_C$ (CDCl$_3$) 172.3, 168.6, 142.6, 139.4, 138.9, 137.7, 123.3, 120.0, 118.7, 117.6, 80.2, 79.4, 76.5, 68.0, 67.4, 65.9, 48.1, 45.4, 36.7, 35 7, 34.3, 33.8, 22.1, 19.7, 15.5 ppm.

EXAMPLE 3

Oxidation of compound 6 of GB-A-2 170 499 (10mg) by the procedure described in Example 1 yielded the 22-keto derivative (5 mg) which was purified by preparative tlc (Silica eluted with ether/hexane, 60:40) $^m$/z (FAB, Na+/Noba) 707 [MNa]+. HPLC Retention time 15 min (25 cm×4.6 mm ultrasphere ODS, Methanol/water (90:10), 1 ml/min.). The 22-keto derivative (5 mg) was dissolved in methanol (5 ml) and an excess of an aqueous solution of hydroxylamine hydrochloride added. The solution was stored at 5° for 2 days and hplc, using the above conditions, indicated the presence of two new products, the 'syn' and 'anti' isomers of the title compound with retention times of 8.7 and 9.1 mins. The mixture was poured into water, extracted with dichloromethane, and the extracts dried (MgSO$_4$) and evaporated. The crude product was used directly in the following reaction.

The crude oxime from above was dissolved in dichloromethane (5 ml) and triethylamine (1 ml). 4-Nitrobenzenesulphonyl chloride (30 mg) was added in portions until hplc indicated that all the oxime had reacted The solution was evaporated, the residue dissolved in methanol and 4-toluenesulphonic acid (30 mg) added. The reaction mixture was stored at 5° for 15 h, evaporated and the residue dissolved in dichloromethane. The solution was washed with aqueous sodium bicarbonate solution, dried and evaporated. Preparative tlc (silica eluted with 80:20 ether/petrol) gave a pure sample of VS 47709 (1 mg), $^m$/z (FAB Na+/Noba) 481 [MNa]+.

EXAMPLE 4

(24R,25R)-22,23-Didehydro-24,25,dimethyl-X

To a solution of (3R*,4R*)-3-methyl-4-(tetrahydropyran)-2-yloxy)-1-pentyne (110 mg, 0.6 mmole) in THF (5 ml) at −78° C. under nitrogen was added butyllithium (1.6M in hexane; 0.32 ml, 0.5 mmole) and the mixture was stirred at −78° C. for 1½ h. A solution of VS 47709 (90 mg, 0.2 mmole) in THF (1 ml) was added to the mixture which was then stirred at −78° C. for 3 h. The reaction was quenched with dilute aqueous ammonium chloride (5 ml) and the mixture was then allowed to warm to 0° C. The aqueous phase was extracted with diethyl ether (2×20 ml) and the combined organic extracts were washed with water (10 ml), dried (MgSO$_4$) and evaporated to give a crude product (150 mg).

A solution of this crude product (150 mg) in ethyl acetate (20 ml) was hydrogenated over Lindlar catalyst (90 mg) for 16 h. The mixture was filtered through celite and evaporated to an oil.

To the unpurified product was added methanol (10 ml) and dilute hydrochloric acid (1M, 1 ml). The mixture was stirred for 1 h and evaporated to dryness to give the crude product. The residue was purified by preparative t.l.c. (silica plates eluted with ethyl acetate:-hexane 30:70) to give the title compound (10 mg); m/z (FAB Na+/NOBA) (relative intensity) 563 [M+Na]+ (100%); $\delta_C$ (CDCl$_3$) 174.0, 142.5, 139.7, 137.0, 136.0, 135.5, 127.5, 123.5, 120.8, 119.4, 118.3, 96.2, 80.3, 77.4, 77.0, 68.6, 68.3, 68.2, 65.6, 57.8, 48.5, 45.6, 40.4, 36.3, 35.9, 34.9, 32.9, 22.3, 19.9, 17.9, 15.5, 12.1 ppm.

EXAMPLE 5

(24S,25R)-22,23-Didehydro-24,25-dimethyl-X and (24R,25S)-22,23-didehydro-24,25-dimethyl-X In a similar manner to Example 4, (3R*,4S*)-3-methyl-4-(tetrahydropyran-2-yloxy)-1-pentyne (152 mg. 0.84 mmole) and VS 47709 (100 mg, 0.21 mmole) gave two products (24S,25R) and (24R,25S)-22,23-didehydro-24,25-dimethyl-X as a mixture. Purification by preparative HPLC gave (24R,25S)-22,23-didehydro-24,25-dimethyl-X (3.9 mg); m/z (FAB Na+/Noba) (relative intensity) 563 [MNa+] (100%); and (24S,25R)-22,23-didehydro-24,25-dimethyl-X (22.0 mg); m/z (FAB Na+/Noba) (relative intensity) 563 [MNa+] (100%); $\delta_C$ (CDCl$_3$) 173.8, 142.6, 142.4, 139.7, 137.1, 135.9, 135.4, 127.9, 123.5, 120.7, 119.4, 118.3, 95.7, 80.3, 77.4, 76.9, 69.7, 68.4, 68.3, 68.2, 57.8, 53.4, 48.5, 45.6, 40.3, 36.3, 36.1, 35.9, 34.8, 22.3, 19.9, 19.0, 16 6, 15.5 ppm.

PREPARATION 1

(3R*,4R*)-3-Methyl-1-pentyn-4-ol

Prepared as described in the literature from trans-2,3-epoxybutane and lithium acetylide, ethylenediamine complex in dimethylsulphoxide (*J Am Chem Soc* (1970) 101, 5367).

PREPARATION 2

(3R*,4R*)-3-Methyl-4-(tetrahydropyran-2-yloxy)-1-pentyne

To dihydropyran (1.3 g) cooled in an ice bath was added (3R*,4R*)-3-methyl-1-pentyn-4-ol (1.3 g) followed by concentrated hydrochloric acid (1 drop) and the mixture was stirred for 16 h at room temperature. Potassium carbonate (100 mg) was added and the mixture stirred for 15 minutes. Diethyl ether (10 ml) was added and the mixture was filtered before evaporation to an oil. The residue was distilled to give the title compound (1.2 g) (b.p. 130°-5° C. at 10 mm Hg).

PREPARATION 3

(3R*,4S*)-3-Methyl-1-pentyn-4-ol

To a suspension of lithium acetylide ethylenediamine complex (4 g, 44 mmole) in dimethyl sulphoxide (10 ml) was added cis-2,3-epoxybutane (2.9 g, 40 mmole) and the mixture was stirred under nitrogen for 10 days at room temperature. The reaction was quenched with water (25 ml) and extracted with diethyl ether (3×50 ml). The combined ethereal extracts were dried (MgSO$_4$) and evaporated to give an oil. The residue was distilled to give the title compound as a colourless oil (1.2 g) (b.p. 35°-45° C. at 30 mm Hg).

PREPARATION 4

(3R*,4S*)-3-Methyl-4-(tetrahydropyran-2-yloxy)-1-pentyne

In a similar manner to Preparation 2 (3R*,4S*)-3-methyl-1-pentyn-4-ol gave the title compound as a colourless oil (1.2 g) (b.p. 115°-20° C. at 40 mm Hg).

REFERENCE EXAMPLE 1

Culture

Streptomyces sp. NCClB 12509 as described in EP-A-0 254 583 (U.S. Ser. No. 076,274) was maintained as vegetative mycelium stored in liquid nitrogen.

1st Stage Seed 100 mls Medium Y was sterilised in 500ml Erlenmeyer flasks closed with cotton gauze caps.

| Medium Y contained:- | |
|---|---|
| *Special Peptone | 0.25% |
| *Lab Lemco | 0.25% |
| *Tryptone | 0.25% |
| *Neutralised Soya Peptone | 0.25% |
| *Malt Extract | 0.25% |
| Soluble Starch | 0.25% |
| Glucose monohydrate | 0.25% |
| Glycerol | 0.25% |
| ∅Trace elements solution | 10 ml/liter |
| pH was unadjusted | |
| ∅The trace elements solution contained:- | |
| CaCl$_2$.2H$_2$O | 1.0% |
| MgCl$_2$.6H$_2$O | 1.0% |
| NaCl | 1.0% |
| FeCl$_3$ | 0.3% |
| ZnCl$_2$ | 0.05% |
| CuCl$_2$.2H$_2$O | 0.05% |
| MnSO$_4$.4H$_2$O | 0.05% |
| CoCl$_2$.6H$_2$O | 0.05% |

(*These products were supplied by Oxoid Ltd., Basingstoke, Hants. UK)

One flask of Medium Y was inoculated with the contents (1.5 ml) of one ampoule of preserved culture. The flask was incubated at 25° C. on a gyratory shaker at 240 rpm for 48 hours.

2nd Stage Seed

Seed Medium C was sterilised in 100 ml amounts in 500 ml Erlenmeyer flasks closed with cotton gauze caps.

| Medium C contained: | |
|---|---|
| Arkasoy 50 | 1.0% |

-continued

| | |
|---|---|
| Glucose monohydrate | 2.0% |
| Spray dried Corn Steep Liquor | 0.5% |
| NaCl | 0.3% |
| pH adjusted to 6.8. | |

(Arkasoy 50 was supplied by British Arkady Co. Manchester, UK).
(Corn Steep Liquor was supplied by Roquette UK Ltd., Tunbridge Wells, Kent, UK).

Flasks of medium C were inoculated with 4% of the 1st stage seed inoculum. These were incubated at 26° C. on a gyratory shaker at 240rpm for 72 hours.

3rd Stage Seed 15 liters of Medium C together with Polypropylene glycol (P2000) 0.1% v/v were sterilised in a 20 liter Biolafitte fermenter (Biolafitte, Poissey, France) The fermenter was fully baffled and fitted with three vaned-disc impellers. Sterile air was supplied at 1 v.v.m and agitation was at 200 rpm.

The contents of two second-stage seed flasks were used to inoculate one 20 liter fermenter and incubation, at 26° C., was for 48 hours.

4th Stage Seed 100 liters Medium C was sterilised at 121° C. in a 150 liter Braun fermenter (B. Braun, Melsungen, W.Germany). 0.1% Antifoaming agent was included with the medium and consisted of 10% pluronic L81 in soybean oil.

(Pluronic L81 was supplied by Blagden-Campbell Chemical Co., Croydon, UK).

The fermenter was fully baffled and fitted with three vaned-disc impellers. Agitation was at 120 rpm and sterile air supplied at 1 v.v.m. The fermenter was inoculated with 4 liters of the 3rd stage seed and incubated at 28° C. for 48 hours.

Fermentation Stage 3000 liters of Medium F1 was sterilised in a 4500 liter Bioengineering fermenter (Bioengineering-Wald, Switzerland).

| Medium F1 contained:- | |
|---|---|
| Arkasoy 50 | 1.0% |
| Glucose monohydrate | 2.0% |
| Dextrin 07005 | 2.0% |
| Casein | 0.2% |
| MgSO$_4$ | 0.1% |
| CaCO$_3$ | 0.5% |
| 10% Pluronic L81 in soybean oil | 0.1% |

(Dextrin 07005 was supplied by Corn Products Ltd., Manchester, UK)
(Casein was supplied by Oxoid Ltd, Hants., UK).

The fermenter was fully baffled and fitted with three, vaned-disc impellers. Sterile air was supplied at 0.5 v.v.m.

The fermenter was inoculated with 100 liters of fourth stage seed inoculum and incubated at 26° C. The agitation rate was maintained at the following rates:

| | |
|---|---|
| 0-2 days | 50 rpm |
| 2-3 days | 75 rpm |
| 3 days-harvest | 100 rpm |

The fermentation ran for 17 days and extra shots of antifoaming agent were added on demand.

Isolation Procedure

At harvest whole broth was transferred to a separate stirred vessel and 10% v/v butan-1-ol was added. The mixture was stirred for 16 hours at 7° C. Thereafter the whole broth (2339 liters) was fed at 5 liters/minute, together with butan-1-ol at 1.7 liters/minute through an in-line static mixer to a Westfalia SA7-03-076 liquid/liquid/solid centrifugal separator (Westfalia Separator Ltd., Oelde, W. Germany). The accumulated solids were discharged intermittently as required.

The raffinate and mycelial solids were combined and submitted to a second, similar extraction with butan-1-ol. Combined butanol extracts were concentrated in vacuo to 20 liters. 40 liters petroleum spirit (60°-80°) was added to preciptitate pigmented impurities which were removed by centrifugation. The supernatant was concentrated in vacuo to 15 liters.

Chromatographic Purification

The concentrate was chromatographed on a column (600 mm diameter × 200 mm) of silica gel (Riedel de Haen, Seelze, W. Germany, 32–63 μm), eluting with a step gradient of ethyl acetate in petroleum spirit (60°-80°). Fractions obtained using >8% ethyl acetate, containing VM 47704 and other active material were set aside. All of the remaining milbemycin—containing fractions were rechromatographed on a similar column, resulting in the separation of a further quantity of VM 47704 and other active material which was combined with that already obtained and evaporated to an oily concentrate (208 g).

This was again chromatographed on silica gel (150 mm × 180 mm column), eluting with a step gradient of ethyl acetate in petroleum spirit (60°-80°), using 3.3 liters pure petroleum spirit, followed by 6.6 liters each of 15%, 25%, 30%, 35% and 40% v/v ethyl acetate in petroleum spirit. The first 25 liters of eluate was discarded, thereafter fractions of 2 liters were collected. Fractions 3–8 were combined and concentrated to an oil.

This material was chromatographed on a column (75 mm diameter × 500 mm) of Sephadex ® LH 20 (Pharmacia, Milton Keynes, UK) using methanol as eluant. All fractions containing milbemycin components were combined.

Further purification was achieved using chromatography on reverse-phase silica. Matrex ® C$_{18}$ silica, 20–45 μm, 60A pore size (Amicon, Stonehouse, UK) was used for all subsequent columns.

Product obtained from the Sephadex ® LH 20 column was chromatographed on a 100 mm diameter × 180 mm column of C$_{18}$ silica, eluting with 85% methanol. The first 1 liter of eluant was discarded, thereafter 20 × 100 ml fractions, all containing milbemycin components were collected and combined.

The solution so obtained was chromatographed on a similar column, eluting firstly with 85% methanol, then with 87.5% methanol. After discarding the first 1 liter of eluate, 36 fractions each of 85 ml, containing active material other than VM 47704 were collected. Thereafter elution was with 87.5% methanol with eluted VM 47704 admixed with other active material.

The latter fractions were chromatographed on a 100 mm diameter × 260 mm column (designated 22I), eluting with 85% methanol. 100 ml fractions were collected. Enrichment of VM 47704 was observed in fractions 42-55. Fractions 35-41 contained additional product.

Fractions 42-55 from column 22I were chromatographed on a similar column (designated 22J), eluting with 82.5% methanol. The first 7.2 liters was discarded then 100 ml fractions were collected. The majority of the VM 47704 was found in fractions 66-85 and further, less pure, product was present in fractions 57-65.

The less pure fractions from columns 22I and 22J were combined and chromatographed on a column (80 mm diameter ×600 mm) using 81% methanol as eluant. The first 9.3 liters were discarded then 100 ml fractions were collected. Fractions 76-86 containing predominantly VM 47704 were combined with fractions 66-85 from column 22J and chromatographed on the same column, using 79% methanol as eluant. The first 20 liters were discarded then 100 ml fractions were collected. Fractions 34-55 were evaporated to dryness to give 209 mg VM 47704.

Characterisation Data for VM 47704

Mass (Electron Impact Mass Spectroscopy) [M]+ = 684; $\delta 13_C$ (CDCl$_3$) 173.0, 172.9, 142.9, 139.1, 137.1, 136.4, 134.0, 123.6, 123.3, 121.7, 120.54, 120.47, 98.8, 81.9, 80.3, 79.0, 71.5, 68.8., 68.4, 67.9, 64.6, 64.1, 48.4, 45.5, 43.2, 36.8, 36.4, 36.3, 35.9, 34.6, 32.0, 25.6, 22.4, 22.2, 17.4, 15.5, 13.1, 10.9.

REFERENCE EXAMPLES 2 AND 3

The seed stages and fermentation stages were carried out as in Reference Example 1, except that in the fermentation stage the agitation was maintained at the following rates:

| 0-3 days | 50 rpm |
| 3 days-harvest | 100 rpm |

The fermentation broth was harvested after 404 hours. Whole broth was discharged from the fermenter and saturated with butanol. Product was extracted with ⅓ volume butanol using an in-line static mixer followed by the Westfalia liquid/liquid/solid separator. The broth was processed at 5 l /min resulting in ca 80% yield. A second, similar, extraction was performed to give essentially quantitative recovery.

Combined butanol extracts were combined, concentrated to low volume (19 l) and 2 volumes of petroleum spirit (60°-80°) were added to precipitate pigmented impurities. Reconcentration resulted in 10.8 l brown oil which was chromatographed on 28 kg silica gel packed in a 600 mm diameter column. Elution was carried out using increasing concentrations of ethyl acetate (up to 50%) in petrol.

Fractions containing VM 48130 and VM 48633 were identified and subjected to further chromatography.

VM 48130 (Reference Example 2) and VM 48633 (Reference Example 3)

A 1.8g fraction containing VM 48130 and VM 48633 was subjected to preparative reverse phase HPLC using a Dynamax-60A C-18 column (500×21.4 mm, Rainin Instrument Company, USA), eluted with a methanol:water gradient at 10 ml/min (82:18 methanol:water rising to 100% methanol over 140 min), monitored by UV spectroscopy at 244 nm. VM 48130 and VM 48633 were detected in the same fractions which were pooled and the solvent evaporated to yield 97.4 mg of material. This was further purified by preparative silica HPLC using a Dynamax-60A Si column (250×21.4 mm, Rainin Instrument Company, USA), eluted with a hexane-:acetone gradient (87:13 to 82:18 over 120 min at 10 ml/min). Fractions were collected and identified by TLC (silica gel plates run with 60:40 hexane:acetone).

This produced substantially pure VM 48633 (4.9 mg; $\lambda_{max}$ (CH$_3$OH) 244 nm, mass (FAB Na+/NOBA) [MNa]+ = 705, $\delta 13_C$(CDCl$_3$) 173.2, 166.4, 157.8, 142.9, 139.2, 137.2, 136.8, 134.1, 123.7, 123.4, 121.4, 120.6, 120.5, 115.6, 98.9, 81.9, 80.3, 79.1, 71.6, 68.8, 68.5, 68.0, 64.7, 63.5, 48.5, 45.6, 36.9, 36.45, 36.37, 36.0, 34.6, 32.1, 27.5, 22.3, 20.3, 17.5, 15.5, 13.1, 10.9 ppm.

Fractions containing VM 48130 (10.6 mg) required final purification by semipreparative HPLC (Hypersil 5 µm ODS 250×10 mm column, HPLC Technology Ltd), eluted with a methanol:water gradient (77:23 methanol:water, rising to 85.15 over 60 min, flow 3 ml/min), monitored by UV spectroscopy at 244 nm. This yielded 4.1 mg of substantially pure VM 48130; $\lambda_{max}$·(CH$_3$OH) 244 nm, mass (FAB, Na+/NOBA) [MNa]+ = 693; $\delta 13_c$ (CDCl$_3$) 177.8, 173.7, 142.8, 139.5, 137.9, 137.4, 133.1, 124.9. 123.4, 120.4, 120.3, 118.1, 100.2, 80.2, 79.2, 76.0, 75.4, 68.5, 68.1, 67.7, 48.5, 45.7, 37.7, 36.21, 36.14, 36.0, 34.6, 34.3, 22.3, 19.9, 19.2, 19.0, 15.6, 13.2, 13.0, 10.8 ppm.

They have retention times of 12.3 min (VM 48130) and 12.9 (VM 48633) when subjected to HPLC under the following conditions: Ultrasphere ODS 5 µm column 250×4.6 mm (Altex) eluted with methanol:water (85.15) at a flow rate of 1 ml/min and monitored by UV spectroscopy at 244 nm.

Temperatures given in the Examples are in Celsius unless otherwise indicated.

We claim:

1. A compound of formula III:

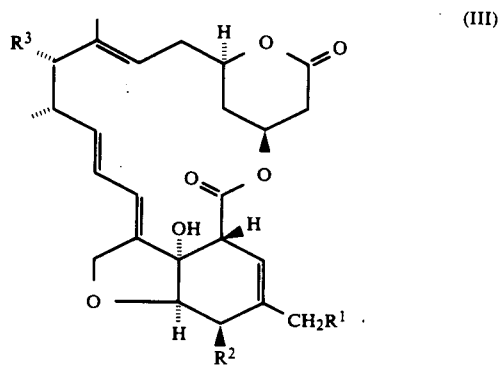

(III)

wherein R$^1$ is hydrogen or optionally protected hydroxy; R$^2$ is alkoxy, optionally protected hydroxy, oxo or C$_{1-6}$ alkyl or C$_{2-6}$ alkenyl O-substituted oximino; R$^3$ is hydrogen, optionally protected hydroxy, or a group 4'-(a-L-oleondrosyl)-a-L-oleandroxylloxy or a-L-oleandrosyloxy wherein the terminal hydroxy group is optionally protected.

2. A process for the preparation of a compound of formula (III) as defined in claim 1, which process comprises treating a compound of formula V:

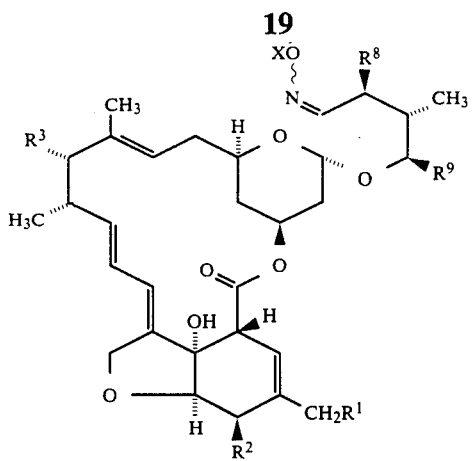

(V) with an acid catalyst to effect Beckmann rearrangement, wherein X is hydrogen or a sulphonyl group, $R^1$ to $R^3$ are as defined in claim 1, $R^8$ is hydrogen or optionally protected hydroxy, and $R^9$ is methyl, ethyl, 1-methyl propyl or (Z) but-2-en-2-yl, with the provision that (a) if $R^1$ is optionally protected hydroxy, then $R^3$ is hydrogen, $R^8$ is hydrogen, and $R^9$ is (Z) but-2-en-2-yl, (b) if and only if $R^3$ is not hydrogen then $R^9$ is 1-methyl propyl, (c) if $R^3$ is not hydrogen, then $R^8$ is optionally protected hydroxy, (d) if $R^9$ is (Z) but-2-en-2-yl and $R^8$ is optionally protected hydroxy, then $R^1$ is hydrogen and $R^2$ is optionally hydroxy, and (e) is $R^2$ is not methoxy or optionally protected hydroxy, then $R^1$, $R^3$ and $R^8$ are hydrogen and $R^9$ is (Z) but-2-en-2-yl.

* * * * *